United States Patent [19]

Ichihashi

[11] Patent Number: 5,141,304
[45] Date of Patent: Aug. 25, 1992

[54] OPHTHALMOLOGICAL MEASUREMENT APPARATUS HAVING SENSITIVITY ERROR CORRECTION

[75] Inventor: Tadashi Ichihashi, Hachioji, Japan

[73] Assignee: Kowa Company Ltd., Japan

[21] Appl. No.: 731,742

[22] Filed: Jul. 16, 1991

[30] Foreign Application Priority Data

Jul. 31, 1990 [JP] Japan ................................. 2-201231

[51] Int. Cl.⁵ .............................................. A61B 3/10
[52] U.S. Cl. ................................... 351/221; 351/205; 128/745
[58] Field of Search ............... 351/205, 214, 211, 221; 128/633, 745; 606/4, 5, 6

[56] References Cited

U.S. PATENT DOCUMENTS 4,957,360 9/1990 Kakizawa .............................. 351/221

*Primary Examiner*—Rodney B. Bovernick
*Attorney, Agent, or Firm*—Bruce L. Adams; Van C. Wilks

[57] ABSTRACT

An ophthalmological measurement apparatus which projects a laser beam into a subject's eye and conducts a prescribed ophthalmological measurement based on the state of laser light scattering in the eye comprises a laser beam projection system for converging a laser beam from a laser source at a measurement point in the eye, a light receiving system for receiving scattered laser light from the interior of the eye by a photosensor means thereof and detecting the light scattering state inside the eye from the measured number of pulses output by the photosensor means. In this arrangement, the sensitivity of the photosensor means is measured, and the result of the light scattering state detection is automatically corrected according to the measured sensitivity of the photosensor means so that accurate ophthalmological measurement results can be obtained notwithstanding aging of the photosensor means or changes in its environmental conditions.

4 Claims, 6 Drawing Sheets

OPHTHALMOLOGICAL MEASUREMENT APPARATUS HAVING SENSITIVITY ERROR CORRECTION

BACKGROUND OF THE INVENTION

1. Field of the Invention

This invention relates to an ophthalmological measurement apparatus, and more particularly to an ophthalmological measurement apparatus which irradiates the interior of a patient's eye with a beam of laser light and uses the laser beam scattered from the interior of the eye to output measurement quantities such as the protein concentration in the oculi anterior.

2. Description of the Prior Art

Measurement of protein concentration in the oculi anterior is of considerable importance in determining whether the camera oculi is inflamed, that is, whether the blood-aqueous barrier function is normal or not. In one method that is frequently used for this, a slit lamp microscope is employed to grade the concentration by observation with the naked eye.

Data obtained with the conventional method of naked-eye measurement lacks reliability as judgments vary depending on the person making the measurement. One solution has been to use a method in which a beam of laser light is projected into the eye and the light scattering from the eye is detected and subjected to quantitative analysis.

This method is disclosed, for example, in Japanese Patent Public Disclosures Nos. 120834/87 (corresponding to U.S. Pat. No. 4,957,360) and 135128/88 (corresponding to U.S. Pat. No. 4,832,043). In an ophthalmological measurement apparatus which employs this method of irradiating the eye with a beam of laser light and detecting the light scattered from the eye, the beam from a laser light source is focused on a prescribed point in the eye such as in the oculi anterior, for example, and scattered light from the eye is detected, via a mask with a rectangular aperture of a prescribed size, by a photosensor which converts the light to an electrical signal which is processed to determine the protein concentration in the oculi anterior or other such ophthalmological measurement quantities.

As the photosensor for detecting the scattered light in the aforesaid conventional ophthalmological measurement apparatus there is used a photomultiplier.

Although photomultipliers are adjusted to a prescribed sensitivity at the time of manufacture, the sensitivity tends to vary with the passage of time and the use environment (particularly the temperature). When a photomultiplier is applied for measuring the intensity of scattered light, as in the case where it is used in the measurement of protein concentration in the oculi anterior, such changes in sensitivity lead to measurement error which degrades the measurement accuracy.

SUMMARY OF THE INVENTION

An object of the present invention is therefore to provide an ophthalmological measurement apparatus which compensates for any variation in the sensitivity of the photomultiplier, thereby ensuring that ophthalmological measurement can be conducted with high accuracy.

In accordance with the present invention the above object is achieved by an ophthalmological measurement apparatus which projects a laser beam into a subject's eye and conducts a prescribed ophthalmological measurement based on the state of laser light scattering in the eye, comprising: a laser beam projection system for converging a laser beam from a laser source at a measurement point in the eye; a light receiving system for receiving scattered laser light from the interior of the eye by a photosensor means thereof and detecting the light scattering state inside the eye from the measured number of pulses output by the photosensor means; means for measuring the sensitivity of the photosensor means; and means responsive to the output of the sensitivity measuring means for correcting the result of the light scattering state detection by the light receiving system.

With the above arrangement, the result of the light scattering state detection can be corrected according to the sensitivity of the photosensor means measured by the sensitivity measuring means.

BRIEF DESCRIPTION OF THE DRAWINGS

The purposes and features of the present invention will become more apparent from a consideration of the following detailed description taken in conjunction with the accompanying drawings in which.

DETAILED DESCRIPTION OF THE PREFERRED EMBODIMENTS

Figure 1:
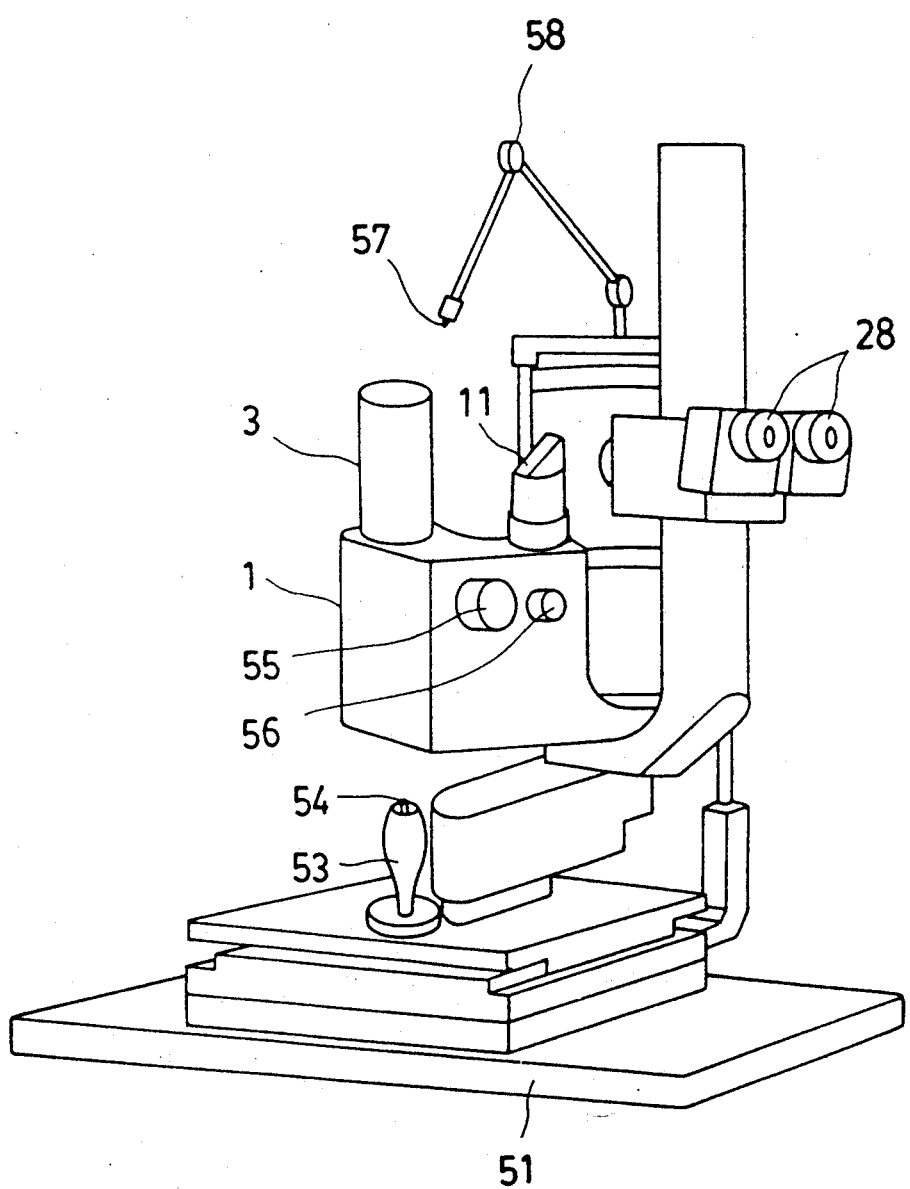
FIG. 1 is a perspective view of an embodiment of the ophthalmological measurement apparatus of the present invention.

The invention will now be described in detail on the basis of the preferred embodiments illustrated in the drawings.

Figure 2:
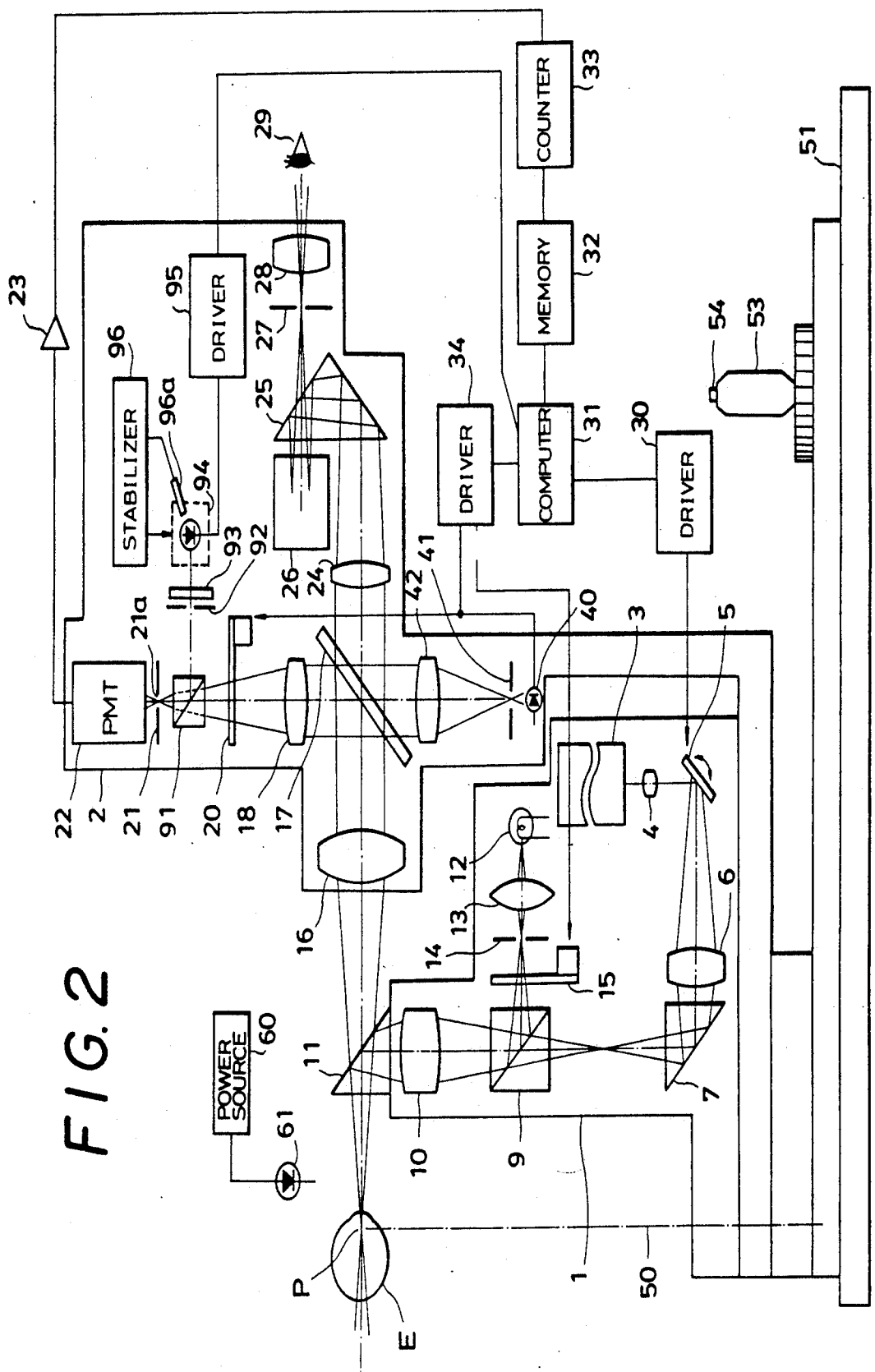
FIG. 2 is a schematic view of the internal configuration of the projection section of the apparatus shown in FIG. 1.
Figure 3:
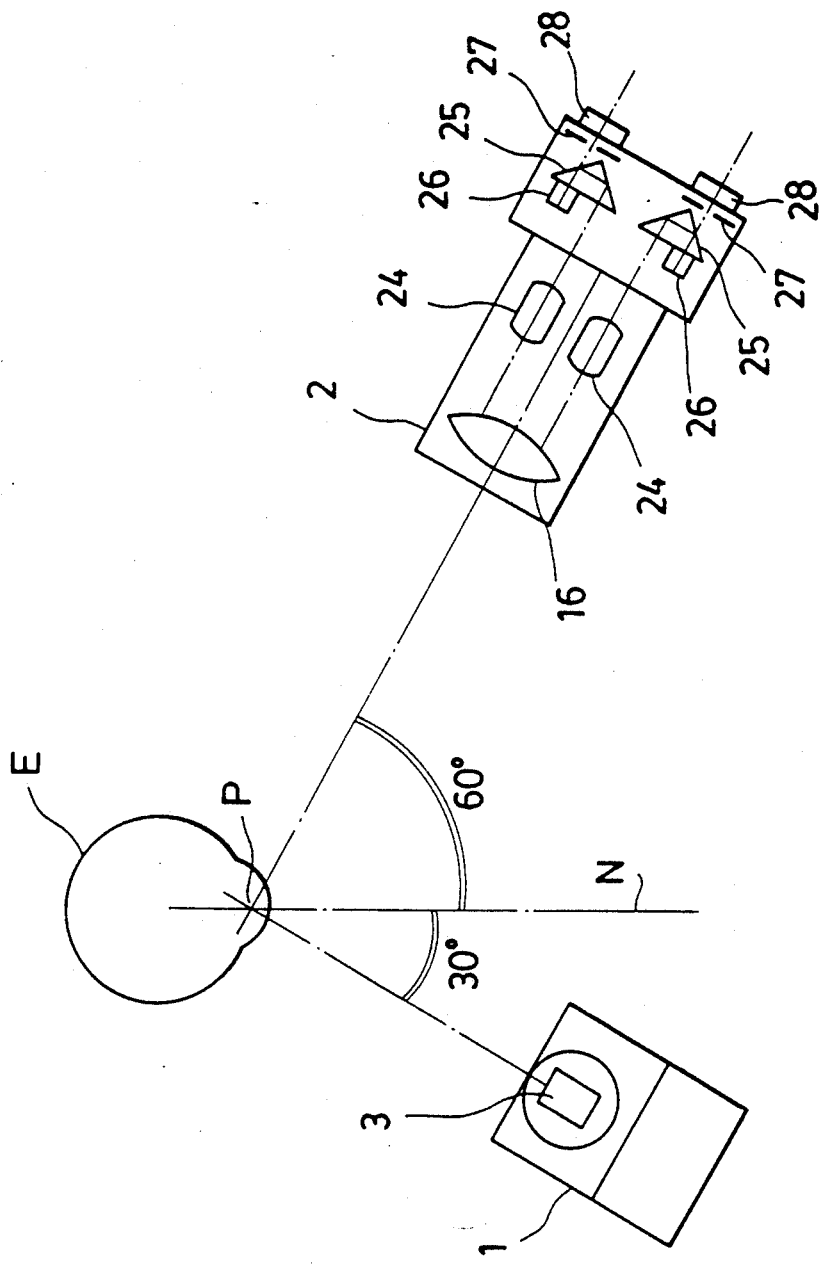
FIG. 3 shows the positional relationship between the light projection section and the light receiving section during measurement.

FIGS. 1 to 3 show the general configuration of an embodiment of the ophthalmological measurement apparatus of this invention. In the drawings reference numeral 1 denotes a laser light projection section having a helium-neon or other such laser light source 3. The laser beam from the laser light source 3 passes through a lens 4, a movable mirror 5, a lens 6, a prism 7, a beamsplitter 9, a lens 10 and a prism 11, whereby the beam is converged on a prescribed point P in the oculi anterior of the eye E being examined.

The movable mirror 5 is connected to a mirror drive circuit 30 controlled by a computer 31 constituted by a microprocessor or the like in a configuration that allows the angle of the movable mirror 5 to be changed so as to deflect the laser beam to scan a measurement zone over a prescribed range about a center formed by a point of laser beam convergence P. As described below, this scanning range is set so that it exceeds the range of an aperture formed in a measurement mask.

The laser light projection section 1 is provided with a white-light source 12 (a halogen lamp), light from which illuminates a slit 14 via a lens 13. The light from the slit 14 thus illuminated passes via a slit light shutter 15, the beam splitter 9, the lens 10 and the prism 11 to form a slit image in the vicinity of the point of convergence P in the oculi anterior of the eye E.

By illuminating the area around the point of convergence P, the slit image allows the position of the point of convergence P to be readily confirmed when the system is being aligned.

The width and length of the slit 14 can be adjusted by a slit width adjustment knob 55 and slit length adjustment knob 56 (FIG. 1) to enable the apparatus to be utilized also as a slit-lamp microscope.

The computer 31 controls the shutter 15 via a drive circuit 34 so that the shutter 15 is open during alignment and closed during measurement of protein concentration in the oculi anterior. This is accomplished by inserting the shutter 15 into, or retracting it from, the corresponding optical system by operating an input device such as a joystick 53 which is equipped with a push-button switch 54 and provided on a base 51.

Figure 6:
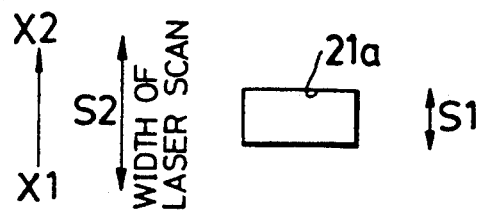

A light receiving section 2 is provided for receiving scattered light from the vicinity of the point of convergence P and to allow the area to be observed. For this, scattered light from the point of convergence P in the oculi anterior of the eye E under examination passes through a lens 16, is reflected by a semitransparent mirror 17 and passes via the lens 18, a photomultiplier shutter 20 and a measurement mask 21 to impinge on a photomultiplier (PMT) 22 which constitutes the photosensor. Light impinging on the photomultiplier 22 is limited to light passing through an aperture 21a formed in the mask 21, which therefore serves to block extraneous light from other areas. The measurement mask 21 (aperture 21a) is provided at a position that is optically conjugate with the point of convergence P, with respect to the light receiving section 2. The aperture 21a is rectangular in shape, as can be seen in FIG. 6.

In this embodiment, a beam splitter 91 is disposed in front of the measurement mask 21 and light from a reference light source 94 is directed onto the light receiving face of the photomultiplier 22 via the beam splitter 91. If convenient, the beam splitter 91 can be replaced with a semi-transparent mirror.

As will be explained in more detail later, the reference light source 94 is used in an operation for compensating for variance in the sensitivity of the photomultiplier 22. A pinhole 92 and a diffusion plate 93 made of semitransparent resin, glass or the like are provided between the reference light source 94 and the beam splitter 91 so that only a prescribed small amount of light reaches the photomultiplier 22. This type of light attenuator is employed in view of the fact that the photomultiplier 22 is used for detecting weak light.

The ambient temperature of the reference light source 94 is regulated by a temperature stabilization circuit 96 so as to maintain the amount of light emitted by the reference light source 94 at a prescribed constant level. The temperature stabilization circuit 96 detects the temperature in the vicinity of the reference light source 94 by means of a thermistor or other such temperature sensor 96a and, in response to the detected temperature, controls a heater 94b or the like for keeping the ambient temperature of the reference light source 94 constant.

The amount of light emitted by the reference light source 94 is controlled by, for example, controlling the amount of current supplied thereto.

The reference light source 94 is turned on and off by the computer 31 via a drive circuit 95.

The output from the photomultiplier 22 is passed through an amplifier 23 and input to a counter 33 which reckons the intensity of the scattered light detected by the photomultiplier 22 as a pulse count per unit time. The count values for each unit time as counted by the counter 33 are stored at specific locations in a memory 32. The data thus stored in the memory 32 is arithmetically processed by the computer 31 to compute the protein concentration in the oculi anterior.

The shutter 20 is provided to protect the photomultiplier 22 and is open only during measurement. Like the shutter 15 it is inserted into, or retracted from, the corresponding optical system by the drive circuit 34 using an input device such as the push-button switch 54 provided on the joystick 53.

Provided to the rear of the semi-transparent mirror 17 of the light receiving section is a microscope system which permits observation around the point of convergence P in the eye. With this configuration, light transmitted through the semi-transparent mirror 17 is observed by an examiner 29 via a lens 24, erect normal prisms 25 and 26, field of vision stop 27 and eyepiece 28. As shown in FIG. 3 the microscope is provided with a double eyepiece for binocular viewing. The microscope allows the projected laser beam and the origin of harmful light rays to be observed prior to measuring the protein concentration in the oculi anterior. To enable harmful light rays to be determined as accurately as possible during system alignment, in this embodiment (as described below in further detail) the measurement zone is scanned at a higher frequency during the alignment than the frequency of the measurement scanning.

The light receiving section 2 is also provided with an alignment index 41 which is illuminated by a light-emitting diode (LED) or other such alignment light source 40. The alignment index 41 is located at a position that is conjugate with the mask 21 and with the field of vision stop 27. Thus, the point of convergence P is conjugate with the mask 21 and field of vision stop 27, and the alignment index 41 is also conjugate with the mask 21 and field of vision stop 27. Similarly to the opening and closing of the slit light shutters 15 and 20, the alignment light source 40 is driven by the drive circuit 34 turn on during alignment and to turn off during measurement.

An eye fixation light 57 constituted, in this embodiment, by a light-emitting diode is provided at a position that permits the examiner to fix the patient's eye (FIG. 1). The eye fixation light 57 can be turned in the direction indicated by the arrow by means of a linkage 58 to enable it to be adjusted to the optimal position relative to the patient undergoing the eye examination. The light selected for the eye fixation light 57 is of a different color than the laser light.

Provided on the base 51 is an input means, which in this case is the joystick 53 equipped with the pushbutton 54. This input means can be used for moving optical elements such as the shutters 15 and 20 into and out of the respective optical system as described above, or may be used to switch the alignment light source on and off. The laser light projection section 1 and light receiving section 2 can each rotate independently in a horizontal plane about an axis 50. With reference to FIG. 3, when the protein concentration in the oculi anterior is being measured a detente mechanism or the like is used to lock the laser light projection section 1 and the light receiving section 2 at an angle of 30 degrees and 90 degrees respectively with respect to the normal of the corneal vertex. When the apparatus is to be used as a slit-lamp microscope the two sections are unlocked to allow them to rotate freely to view the eye in cross-section.

A power supply 60 (FIG. 2) is provided for supplying power to the various components and circuitry. A lamp 61 indicates when the power supply 60 is on.

Measurement processing

The overall operation of the apparatus thus configured will now be described.

The patient's head is positioned on a chin rest, the white-light source 12 is switched on and the shutter 15 is opened to project an image of the slit 14 onto the eye E. The photomultiplier shutter 20 is closed during this alignment procedure. The laser beam from the laser light projection section 1 is converged on the point of convergence P in the eye E, and the mirror driver circuit 30 functions to oscillate the movable mirror 5 so that the laser beam scans the measurement zone at high speed about a center formed by the point of convergence P. As shown in FIG. 6, the scanning width S2 is set to about twice the width S1 of the image of the mask aperture 21a in the eye. The scanning frequency used is 50 to 60 Hz, for instance, which is high enough to permit observation of the measurement zone by the human eye without any perception of flicker.

Figure 4:
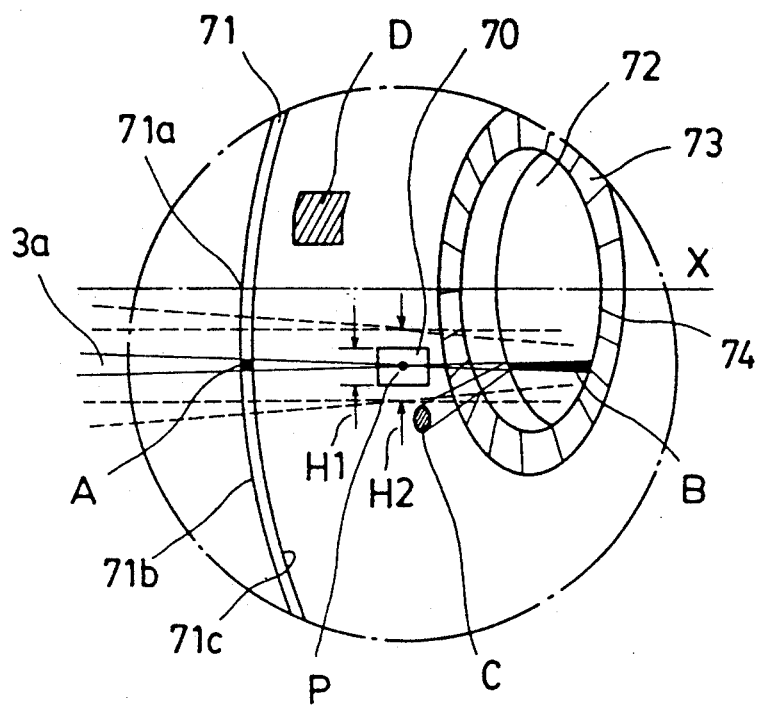
FIG. 4 is an explanatory view of the observed origin of harmful light rays.

Next, the alignment light source 40 is switched on to illuminate the alignment index 41. The image that the examiner will see at this point is shown in FIG. 4. Since the alignment index 41 is in a conjugate relationship with the mask 21 and field of vision stop 27, the point of convergence P is at a position that is conjugate with the mask 21 and the field of vision stop 27. Therefore, the alignment index 41 illuminated by the light source 40 forms images at the field of vision stop 27 and the measurement mask 21, which are points conjugate therewith. Moreover, since the field of vision stop 27 and the measurement mask 21 are conjugate with the point of convergence P, it appears to the examiner 29 that the alignment index 41 is located at the point of convergence P.

Figure 5:
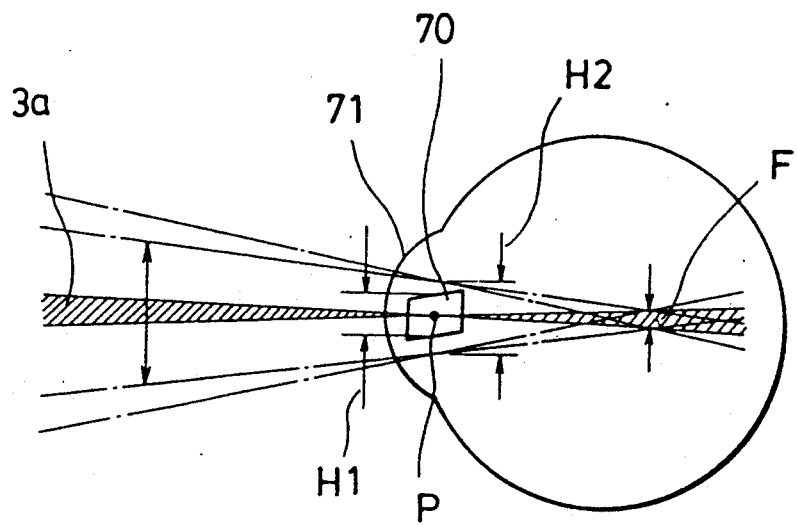
FIGS. 5 and 6 are explanatory views illustrating the range of deflection of the laser beam.

When an arrangement is used whereby the size and shape of the alignment index 41 is such that the image of the alignment index on the mask 21 coincides with the aperture 21a, to the examiner it will appear that the aperture 21a is highlighted at the point of convergence P. In FIGS. 4 and 5 this image of the rectangular aperture 21a is denoted by the reference numeral 70. With reference to FIG. 4, which shows what is actually observed via the eyepiece 28, the aperture image 70 is shown more or less in the middle of the field of vision slightly below the center line X that passes through the corneal vertex 71a. To simplify the explanation, in FIG. 5 the center of the aperture image 70 is shown as coinciding with the vertex of the cornea 71.

In this embodiment the movable mirror 5 scans the laser beam 3a over a range that is about twice the width of the image 70 of the aperture 21a. In the drawings (FIGS. 4 and 5) in which H2 is the range of a measurement zone scan sweep by the laser beam 3a and H1 is the length of the aperture image 70 measured along the short side, H2 is about twice H1. In FIG. 5, F is a point at which there is no movement even during deflection of the laser beam 3a. There is no movement at F because it is conjugate with respect to the axis of oscillation of the reflecting surface of the movable mirror 5, and therefore the oscillation of the movable mirror 5 has no bearing on it.

With reference to FIG. 4, light rays originating in an area outside the aperture image 70 will be unable to pass through the mask 21, and it thus becomes possible to block them by suitably causing the sources of harmful rays of light present within the cornea and the crystalline lens to fall outside the area of the mask aperture image 70. Light rays harmful to the measurement are described below.

The laser beam 3a impinges on the cornea 71 before reaching the point of convergence P and is scattered from the part of the cornea 71 marked A. (Although slit and laser light is actually scattered from two points, the front surface 71b and rear surface 71c of the cornea 71, because of the closeness of the two in the drawing they are shown as a single point A.) The laser beam 3a also passes through the point of convergence P and into the crystalline lens 72 where it produces scattered light B. Moreover, light reflected by the surface of the crystalline lens 72 forms an image C on the cornea 71. This harmful light B and C is particularly intense in the case of a prosthetic crystalline lens. In FIG. 4, 73 is the iris. The boundary between the iris 73 and the crystalline lens 72 forms the pupil 74. At D, a corneal image is formed by scattered light from the exit face of the prism 11. Specifically, as the laser light passes through the prism 11 and converges in the eye, it is scattered at the exit face of the prism, producing secondary light sources that give rise to a spurious image owing to the convex mirror effect of the cornea.

The above A to D are the main sources of harmful rays. For making it possible to distinguish these harmful rays during alignment, in this embodiment, during the alignment the laser beam 3a is made to scan the measurement zone at high speed at the same scan width (H2) used for measurement scanning. Since this high-speed scanning of the measurement zone is performed at a frequency such as 50 Hz or 60 Hz that is above the flicker perception threshold of the human eye, it becomes possible to simulate the harmful light rays arising during actual measurement, which facilitates the identification and elimination of the harmful rays.

The elimination of the harmful light rays A to D is realized by aligning the apparatus so that the rays do not come within the aperture image 70. As these harmful light rays behave like scattered light sources with low directivity and illuminate the surrounding area, in order to ensure that only scattered light from proteins in the oculi anterior is received, the system should be aligned to achieve a maximum separation of the aperture image 70 from the harmful light sources to optimize measurement precision. When the system is aligned in this manner, it becomes possible to receive solely the light scattered by the protein in the oculi anterior and thus to increase the accuracy of the measurement. In this case, if the two colors of the light for illuminating the alignment index are made different from the color of the laser light, the mask aperture image 70 can be readily distinguished from the harmful light ray sources A to D.

Preferably, the aperture image 70 in the eye should have a width that is about one-thirtieth to one-fifteenth the diameter of the dilated pupil and a length that is one-eighth to one-quarter the depth of the oculi anterior. After the above alignment is accomplished, the system mode is changed to measurement. In measurement mode, pressing the switch 54 of the joystick 53 turns off the alignment light source 40, closes the slit light shutter 15, opens the photomultiplier shutter 20 and enables scattered laser light to be received by the light receiving section 2. The protein concentration in the oculi anterior can then be determined by measurement of the received light.

During the measurement process the projection section 1 projects the beam of laser light at the point of convergence P of the eye E under examination and light scattering from the area around the point of convergence P is received by the photomultiplier 22 of the light receiving section 2.

The movable mirror 5 is oscillated by the mirror drive circuit 30 in the direction shown by the arrow to scan the measurement zone with point P at the center. As there is no need to eliminate flicker during measurement scanning, the laser beam 3a is deflected at a lower frequency setting of about 2 Hz. The scanning width at this time is the same as that during alignment, namely about twice the width S1 of the aperture 21a (FIG. 6). The photomultiplier 22 receives incident scattered laser light via the aperture 21a and detects the intensity of the light scattered by protein particles in the measurement zone of the oculi anterior. The scattered light intensity is converted to a corresponding pulse train and counted by the counter 33 as a pulse count per unit time period, and the count values per unit time are stored at specific locations in the memory 32.

Figure 7:
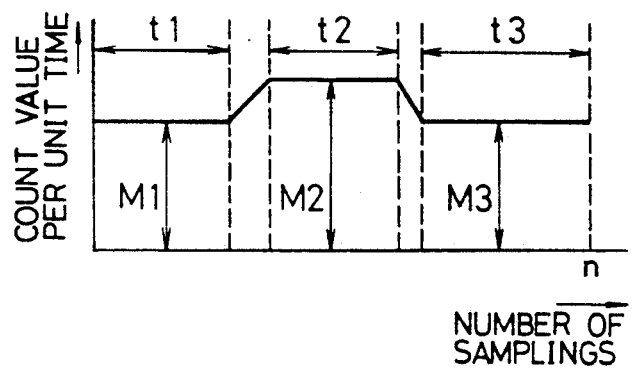
FIG. 7 is a waveform of a signal obtained from one sweep of the scanning laser beam.

As described earlier and shown in FIG. 6, when each scan of the laser beam 3a extends from x1 to x2 and the count values for n scans have been stored at respective memory locations, the count values stored in the memory 32 become as shown in FIG. 7 when arranged in time sequence.

With reference to FIG. 7, t1 and t3 are intervals when the incident laser beam 3a is not within the aperture 21a and indicate the inclusion of noise components produced by intra-ocular reflection or scattering of light other than the aforesaid harmful rays, or the ambient brightness of the measurement environment. M1 and M3 are taken as average values of counts in the memory 32 for intervals t1 and t3. Also included as noise in M1 and M3 is the dark current of the photomultiplier 27. These noise components fluctuate from measurement to measurement.

Interval t2 is the interval during which the scattered laser light enters via the aperture 21a and includes signal components corresponding to the protein concentration in the oculi anterior, noise components caused by reflection and scattering, noise components caused by the ambient brightness, and the photomultiplier dark current. M2 is the average of the count values stored in the memory 32 during this interval.

Figure 8A:
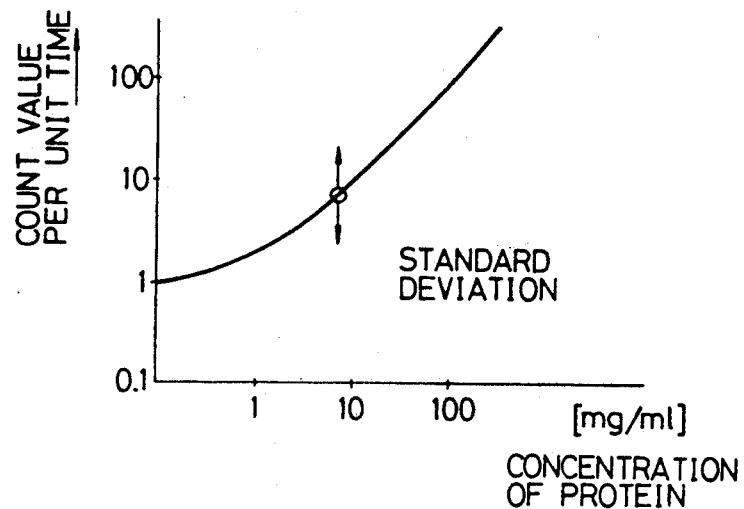
FIGS. 8a and 8b are characteristic curves plotted from data values obtained at different scanning widths.
Figure 8B:
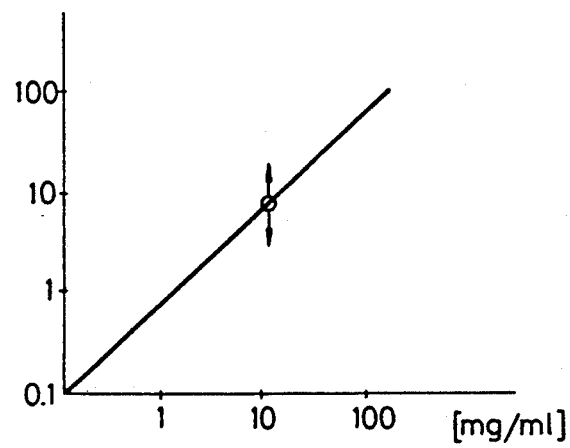

The computer 31 deducts the mean value of M1 and M3 from the value M2 stored in the memory 32 to extract the effective component, from which it computes the protein concentration in the oculi anterior. If the system has been properly aligned, the values of M1 and M3 will be about the same. If the data were only obtained by measurement during the interval t2 the signal/noise ratio would be poor and the variance large with a corresponding degradation in reproducibility (FIG. 8a) but, as shown by FIG. 8b, in accordance with this invention the signal/noise ratio is improved by deducting the noise component, which also increases the dynamic range and improves the reproducibility.

Correction of measurement result

The method used for correcting the measurement result based on the sensitivity of the photomultiplier 22 will now be explained. This process commences after termination of the measurement mode and begins with measurement of the sensitivity of the photomultiplier 22.

At this time, the computer 31 closes the photomultiplier shutter 20 to shield it from ambient light and causes the reference light source 94 to emit the prescribed amount of light. While the reference light source 94 is being driven, it is controlled by the temperature stabilization circuit 96 in accordance with the temperature thereof so as to maintain the amount of light it emits at a prescribed constant level and this prescribed amount of light passes to the photomultiplier 22.

The computer 31 further causes the pulses output by the photomultiplier 22 during a prescribed time period to pass through the amplifier 23 and be counted by the counter 33. The sensitivity of the photomultiplier 22 is calculated on this basis of this count as a ratio with respect to a standard sensitivity which was measured on the same scale and stored in the memory 32 just before the ophthalmological measurement apparatus left the factory. This ratio is then used for correcting the pulse count corresponding to the intensity of the scattered light.

For example, if the standard sensitivity is defined as corresponding to 100 pulses and the number of pulses counted in the sensitivity measurement is 90, the aforesaid ratio with respect to the standard sensitivity becomes 90/100 (=0.9). In order to compensate for this decline in sensitivity it suffices to multiply the number of pulses obtained in the scattered light measurement by the reciprocal of the aforesaid ratio with respect to the standard sensitivity (90/100 (=0.9)) so as to obtain a scattered light measurement result corrected for the photomultiplier sensitivity.

Since the scattered light measurement result can be automatically compensated for the sensitivity of the photomultiplier 22 in the foregoing manner, it becomes possible to obtain stable ophthalmological measurement results over a long period of time, irrespective of aging of the photomultiplier or changes in its ambient conditions (particularly temperature) and without need for carrying out troublesome adjustments.

Moreover, since the amount of light emitted by the reference light source 94 used in compensating for variance in the sensitivity of the photomultiplier 22 is stabilized against temperature variation, the sensitivity of the photomultiplier can be accurately ascertained independently of the ambient conditions, whereby it is in turn possible to carry out the compensation of the scattered light measurement result with high accuracy.

While the foregoing description relates to the case where the ambient temperature of the reference light source 94 is stabilized, if the temperature dependence characteristics of the reference light source 94 are known in advance, it is alternatively possible to control the amount of light emitted by controlling the amount of current supplied to the reference light source 94.

Moreover, instead of carrying out the compensation for the sensitivity of the photomultiplier 22 every time a scattered light measurement is conducted as in the embodiment just described, it is alternatively possible to implement an appropriate operational mode (such as servicing mode) either before or after measurement, in which the sensitivity ratio of the photomultiplier 22 is calculated through a manual operation and stored in the memory 32 in advance for use in correcting the scattered light measurement result.

Figure 9:
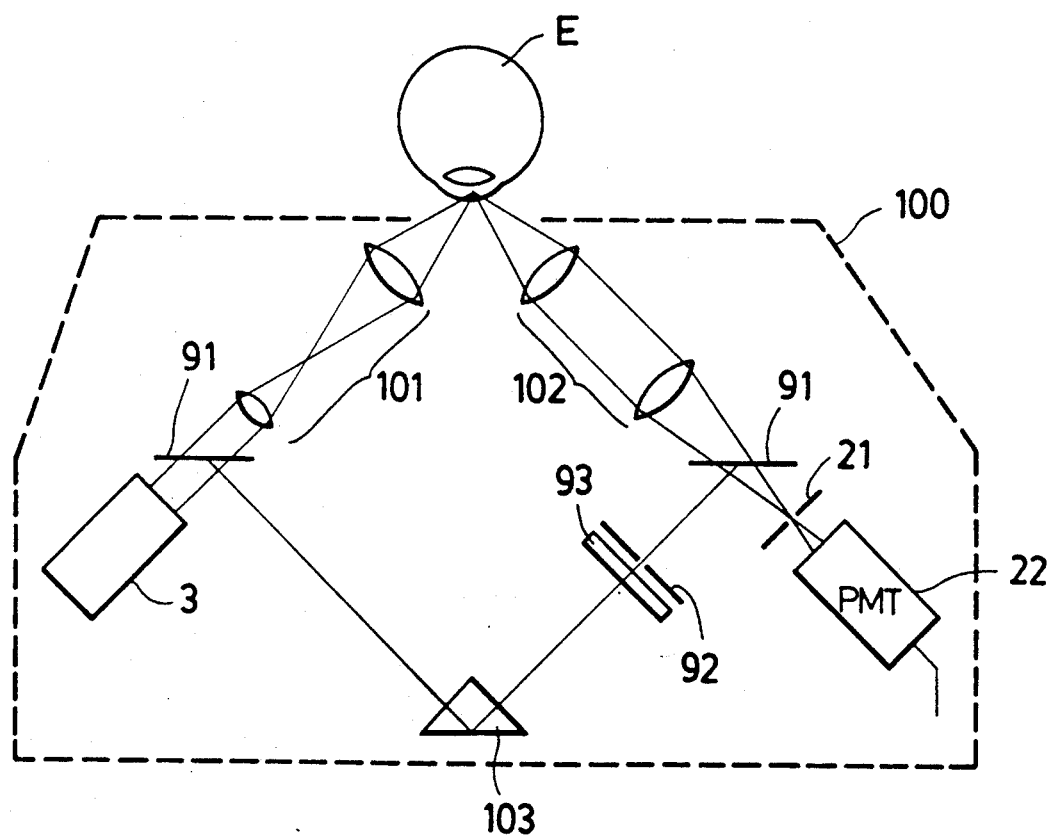
FIG. 9 is an explanatory view showing another embodiment of the ophthalmological measurement apparatus of the invention.

FIG. 9 shows another embodiment of the invention. In the preceding embodiment, the laser light projection section and the light receiving section were constituted as separate units. As shown in FIG. 9, however, it is also possible to integrate the laser light projection section and the light receiving section case 100 and use the laser light source 3 as the reference light source.

In the configuration according to FIG. 9, the light output by the laser light source 3 is split by a 20 semi-transparent mirror 91' and the reflected component thereof passes through a prism 103, the diffusion plate 93, the pinhole 92 and a semi-transparent mirror 91 to enter the photomultiplier 22. (Reference numerals 101 and 102 indicate the aforesaid light projection and light receiving systems shown in simplified form and include, for example, the photomultiplier shutter and the like.

When this arrangement is employed, the output of the photomultiplier 22 at the time the laser light source 3 is operated under prescribed conditions is measured and stored in the memory 32 in advance as a reference measurement value. Then, during measurement or during operation in the servicing mode or the like, the laser light source 3 is again operated under the prescribed conditions and the output of the photomultiplier 22 is measured as a reference measurement value. The sensitivity ratio is then calculated and used for correcting the scattered light measurement result.

The arrangement according to FIG. 9 is advantageous in that it enables the compensation to be carried out not only for sensitivity of the photomultiplier 22 but also for the sensitivity characteristics of the entire measurement system.

The arrangement used for temperature compensation in the preceding embodiment can also be applied for temperature compensation of the amount of laser light emitted in the embodiment according to FIG. 9.

As is clear from the foregoing description, the ophthalmological measurement apparatus according to this invention projects a laser beam into a subject's eye and conducts a prescribed ophthalmological measurement based on the state of laser light scattering in the eye and for this purpose is provided with a laser beam projection system for converging a laser beam from a laser source at a measurement point in the eye, a light receiving system for receiving scattered laser light from the interior of the eye by a photosensor means thereof and detecting the light scattering state inside the eye from the measured number of pulses output by the photosensor means, means for measuring the sensitivity of the photosensor means, and means responsive to the output of the sensitivity measuring means for correcting the result of the light scattering state detection by the light receiving system. With this arrangement, the result of the light scattering state detection can be corrected according to the sensitivity of the photosensor means measured by the sensitivity measuring means, whereby it becomes possible to automatically compensate for any variance in the sensitivity of the photosensor and thus to conduct highly accurate ophthalmological measurement over a long period of time, without need for carrying out troublesome adjustments.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof.Therefore, it is intended that the invention should not be limited to the particular embodiment disclosed as the best mode contemplated for carrying out the invention, but that the invention will include all embodiments falling within the scope of the appended claims.

What is claimed is:

1. An ophthalmological measurement apparatus which projects a laser beam into a subject's eye and conducts a prescribed ophthalmological measurement based on the state of laser light scattering in the eye, comprising:
   a laser beam projection system for converging a laser beam from a laser source at a measurement point in the eye;
   a light receiving system for receiving scattered laser light from the interior of the eye by a photosensor means thereof and detecting the light scattering state inside the eye from the measured number of pulses output by the photosensor means;
   means for measuring the sensitivity of the photosensor means; and
   means responsive to the output of the sensitivity measuring means for correcting the result of the light scattering state detection by the light receiving system.

2. An ophthalmological measurement apparatus as set forth in claim 1, wherein the sensitivity measurement means comprises a reference light source for inputting light to the photosensor means and means for stabilizing the amount of light emitted by the reference light source.

3. An ophthalmological measurement apparatus as set forth in claim 1, wherein the laser source is used as the reference light source of the sensitivity measurement means.

4. An ophthalmological measurement apparatus as set forth in claim 1, further comprising means for blocking disturbance light other than the light beams from the reference light source during sensitivity measurement by the sensitivity measurement means.

* * * * *